United States Patent [19]
Hommeltoft et al.

[11] Patent Number: 6,121,486
[45] Date of Patent: Sep. 19, 2000

[54] RECOVERY OF SULPHONIC ACID ESTERS FROM A HYDROCARBON STREAM

[75] Inventors: Sven Ivar Hommeltoft, Hillerød; Gitte Kobberø Mikkelsen, Måløv; John Zavilla, Kokkedal, all of Denmark

[73] Assignee: Haldor Topsoe A/S, Lyngby, Denmark

[21] Appl. No.: 09/256,736

[22] Filed: Feb. 24, 1999

[30] Foreign Application Priority Data

Feb. 27, 1998 [DK] Denmark ................................. 0262/98

[51] Int. Cl.$^7$ .................................................. C07C 143/00
[52] U.S. Cl. ........................................... 562/115; 562/124
[58] Field of Search ..................................... 562/115, 124

[56] References Cited

U.S. PATENT DOCUMENTS 5,220,095  6/1993  Hommeltoft et al. .
5,245,100  9/1993  Hommeltoft et al. .

FOREIGN PATENT DOCUMENTS 080497  7/1997  Denmark .

*Primary Examiner*—Paul J. Killos
*Attorney, Agent, or Firm*—Ostrolenk, Faber, Gerb & Soffen, LLP

[57] ABSTRACT

A method for hydrolysis of a sulphonic acid ester in a hydrocarbon substrate by aqueous extraction of the hydrocarbon substrate, comprising steps of contacting the hydrocarbon substrate with an aqueous phase containing an ammonia salt, thereby hydrolyzing the sulphonic acid ester to the corresponding sulphonic acid; and recovering the sulphonic acid by separating the aqueous phase from the hydrocarbon substrate.

10 Claims, No Drawings

RECOVERY OF SULPHONIC ACID ESTERS FROM A HYDROCARBON STREAM

FIELD OF INVENTION

The present invention relates to a method for the hydrolysis of a sulphonic acid ester in a hydrocarbon substrate and recovery of the corresponding sulphonic acid. The process of this invention is, in particular, suitable for recovery of an alkyl sulphonic acid ester in acid form from an acid catalyzed alkylation effluent stream.

BACKGROUND OF THE INVENTION

Product streams from acid catalyzed alkylation reactions contain dissolved acid catalyst and small amounts of alkyl esters of the acid catalyst. These compounds have to be removed from the product stream prior to further processing. It is known from DK Patent Application No. 0804/97 to remove (less than 1 ppm) acid compounds and alkyl esters from a hydrocarbon stream by passing the stream through a bed of silicagel wetted with water. The acid can, subsequently, be recovered by washing with water.

Isobutane alkylation is known to be catalyzed by perfluorinated sulphonic acids, including trifluoromethanesulphonic acid (U.S. Pat. No. 5,220,095 and U.S. Pat. No. 5,245,100). Alkyl esters of these acids, e.g. isopropyltriflate (i-PrOTf), are formed as intermediates in the above process and are present in small amounts in the product stream from the alkylation process at typical operation conditions. It is further known to recover triflate esters from the above process by aqueous extraction of the product stream.

DESCRIPTION OF THE INVENTION

We have found that when carrying out hydrolysis of sulphonic acid ester during extraction with water in presence of an ammonium salt, the rate of hydrolysis is increased when compared to the use of water alone. Sulphonic acid esters are in general much more soluble in hydrocarbons than in water, and because of limited contact between the ester and water, even at vigorous stirring, hydrolysis of the ester is very slow. Using a solution of an ammonium salt in water increases the rate of hydrolysis. The increase in hydrolysis rate depends upon the concentration of the ammonium salt.

Pursuant to the above finding, this invention provides a method for hydrolysis of a sulphonic acid ester in a hydrocarbon substrate by aqueous extraction of the hydrocarbon substrate, comprising steps of contacting the hydrocarbon substrate with an aqueous phase containing an ammonia salt, thereby hydrolyzing the sulphonic acid ester to the corresponding sulphonic acid; and recovering the sulphonic acid by separating the aqueous phase from the hydrocarbon substrate.

At present preferred ammonium salts for use in the invention are alkyl ammonium salts and most preferred tri-alkyl and tetra-alkyl ammonium salts.

The invention is, in particular, useful in the recovery of fluorinated alkyl sulphonic acids from effluent streams from acid catalyzed alkylation of hydrocarbons. Thereby, valuable amounts of fluorinated alkyl sulphionc acid cataylyst being present in the effluent in the form of an ester are recovered from the effluent stream and may be reused in the alkylation process.

EXAMPLE 1

Hydrolysis of i-propyltriflate (i-PrOTf) with Water and Triethylammoniumtriflate (TfOHNEt$_3$)

A solution of i-PrOTf in heptane is transferred to a 50 ml autoclave. The solution is slowly heated to the desired reaction temperature. A sample is withdrawn and transferred to a glasflask containing a weighed amount of a solution of ~1 nonane and 30% octylamine (OcNH$_2$) in hexane. The flask is shaken and left for a minimum of 30 minutes. The weight of the sample added is noted. A solution of TfOHNEt$_3$ in water is added to the solution in the flask. The mixture is then stirred and samples of the organic phase are withdrawn and treated with a weighed amount of a solution of 1% nonane and 30% OcNH$_2$ in hexane. The sampling time and the weight of the sample are noted. The mixture in the sample flask is treated with 2 M NaOH(aq). After phase separation, the organic phase is analysed by GC-FID.

In the GC-FID, the amount of isopropyloctylamine is analysed against the internal reference nonane. The amount of isopropyloctylamine is equivalent to the amount of i-PrOTf.

Comparison of the following Examples 2 and 3 shows that a 80% (w/w) of TfOHNEt$_3$ in water is much more efficient for hydrolysis of i-PrOTf than the use of water alone. In Example 2 only water is used resulting in about 60% hydrolysis of i-PrOTf after 20 min. When using a 80% (w/w) of TfLOHNEt$_3$ in water as in Example 3, it is possible to hydrolyze more than 99% of i-PrOTf after 10 min. at 23° C.

Comparison of Examples 3 and 6 shows that more than 99% of i-PrOTf are hydrolysed after 4 min. at 50° C. At 23° C. 99% of i-PrOTf are hydrolysed after 10 min.

Comparison of Examples 3, 4 and 5 shows that a concentration where the rate of hydrolysis is at a maximum. A concentration of ~80%(w/w) TfOHNEt$_3$ results in a faster hydrolysis than concentrations of 40 and 95i(w/w) TfOHNEt$_3$.

Comparison of Examples 2 and 7 shows that tetra-alkyl ammonium salts also increase the reaction rate relative to the use of only water.

EXAMPLE 2

24.55 g of a solution of i-PrOTf in heptane are stirred (~2000 rpm) with water (6 g) at 23° C. The results obtained thereby are summarized in Table 1 below.

TABLE 1

| Time (min) | 0 | 10 | 20 |
|---|---|---|---|
| Conversion in % | | 22.26 | 60.45 |
| i-PrOTf ppm | 23591 | 18340 | 9329 |

EXAMPLE 3

23.6 g of a solution of i-PrOTf in heptane are stirred ~2000 rpm) with a solution of TfOHNEt$_3$ (6.0 g) in water (1.5 g) corresponding to 80% (w/w) TfOHNEt$_3$ at 23° C.

TABLE 2

| Time (min) | 0 | 2 | 5 | 10 | 20 |
|---|---|---|---|---|---|
| Conversion in % | | 83.10 | 96.93 | 99.53 | 99.89 |
| i-PrOTf ppm | 47719 | 8061 | 1464 | 221 | 52 |

EXAMPLE 4

23.64 g of a solution of i-PrOTf in heptane are stirred (~200 rpm) with a solution of TfOHNEt$_3$ (3.01 g) in water (4.54 g) (39.9% (w/w) TfOHNEt$_3$) at 23° C.

TABLE 3

| Time (min) | 0 | 2 | 5 | 10 | 20 |
|---|---|---|---|---|---|
| Conversion in % | | 25.03 | 63.56 | 95.34 | 99.42 |
| i-PrOTf ppm | 63562 | 47652 | 23158 | 2961 | 363 |

EXAMPLE 5

23.72 g of a solution of i-PrOTf in heptane are stirred (~2000 rpm) with a solution of TfOHNEt$_3$ (6.0 g) in water (0.30 g) (95.2% (w/w) TfOHNEt$_3$) at 22° C.

TABLE 4

| Time (min) | 0 | 2 | 5 | 10 | 20 |
|---|---|---|---|---|---|
| Conversion in % | | 32.72 | 58.16 | 84.30 | 97.89 |
| i-PrOTf ppm | 7502 | 5047 | 3138 | 1177 | 158 |

EXAMPLE 6

22.4 g of a solution of i-PrOTf in heptane are stirred (~2000 rpm) with a solution of TfOHNEt$_3$ (6.0 g) in water (1.52 g) at 50° C.

TABLE 5

| Time (min) | 0 | 2 | 5 | 8 | 12 | 20 | 40 | 50 |
|---|---|---|---|---|---|---|---|---|
| Conversion in % | | 96.82 | 99.30 | 99.59 | 99.61 | 99.71 | 99.78 | 100 |
| i-PrOTf ppm | 12678 | 402 | 88 | 52 | 49 | 36 | 28 | 0 |

EXAMPLE 7

24.38 g of a solution of i-PrOTf in heptane are stirred (~2000 rpm) with a solution of TfOHN(C$_3$H$_7$)$_4$(5.81 g) in water (1.52 g) and TfOH (4.22 g) at 23° C.

TABLE 6

| Time (min) | 0 | 2 | 4 | 8 | 15 | 25 | 40 |
|---|---|---|---|---|---|---|---|
| Conversion in % | | 29.37 | 41.01 | 66.57 | 86.52 | 96.41 | 99.41 |
| i-PrOTf ppm | 15152 | 10700 | 8937 | 5065 | 2042 | 544 | 88 |

EXAMPLE 8

24.36 g of a solution of i-PrOTf in heptane are stirred (~2000 rpm) with a solution of TfOHN(C$_6$H$_{13}$)$_3$ (6.00 9) in water (1.11 g) and TfOH (2.51 g) at 23° C.

TABLE 7

| Time (min) | 0 | 2 | 4 | 8 | 15 | 25 | 40 |
|---|---|---|---|---|---|---|---|
| Conversion in % | | 42.79 | 53.06 | 69.11 | 84.85 | 94.46 | 98.73 |
| i-PrOTf ppm | 17741 | 10150 | 8327 | 5480 | 2687 | 982 | 225 |

EXAMPLE 9

24.24 g of a solution of i-PrOTf in heptane are stirred (~2000 rpm) with a solution of (C$_6$H$_{13}$)NH$_3$OTf (6.00 g) in water (2.00 g) at 23° C.

TABLE 8

| Time (min) | 0 | 2 | 4 | 8 | 15 | 25 | 40 |
|---|---|---|---|---|---|---|---|
| Conversion in % | | 80.89 | 96.39 | 99.74 | 99.88 | 99.89 | 100 |
| i-PrOTf ppm | 25420 | 4857 | 916 | 65 | 30 | 26 | 0 |

What is claimed is:

1. A method for hydrolysis of a sulphonic acid ester in a hydrocarbon substrate by aqueous extraction of the hydrocarbon substrate, comprising steps of contacting the hydrocarbon substrate with an aqueous phase containing an ammonia salt, thereby hydrolyzing the sulphonic acid ester to the corresponding sulphonic acid; and recovering the sulphonic acid by separating the aqueous phase from the hydrocarbon substrate.

2. Method of claim 1, wherein the ammonium salt consists of an alkyl ammonium salt.

3. Method of claim 2, wherein the alkyl ammonium salt comprises a tri-alkyl and/or tetra-alkyl ammonium salt.

4. Method of claim 1, wherein the sulphonic acid ester consists of a fluorinated alkyl sulphonic acid ester.

5. Method of claim 4, wherein the fluorinated alkyl sulphonic acid ester is an ester of trifluoromethanesulphonic acid.

6. Method of claim 1, wherein the hydrocarbon substrate consists of alkylate product obtained by fluorinated sulphonic acid catalyst alkylation of hydrocarbon.

7. Method of claim 2, wherein the hydrocarbon substrate consists of alkylate product obtained by fluorinated sulphonic acid catalyst alkylation of hydrocarbon.

8. Method of claim 3, wherein the hydrocarbon substrate consists of alkylate product obtained by fluorinated sulphonic acid catalyst alkylation of hydrocarbon.

9. Method of claim 4, wherein the hydrocarbon substrate consists of alkylate product obtained by fluorinated sulphonic acid catalyst alkylation of hydrocarbon.

10. Method of claim 5, wherein the hydrocarbon substrate consists of alkylate product obtained by fluorinated sulphonic acid catalyst alkylation of hydrocarbon.

* * * * *